(12) United States Patent
Thiel

(10) Patent No.: US 10,514,336 B2
(45) Date of Patent: Dec. 24, 2019

(54) TERAHERTZ MEASURING APPARATUS FOR MEASURING TEST OBJECT AND A TERAHERTZ MEASUREMENT METHOD

(71) Applicant: INOEX GmbH Innovationen und Ausruestungen fuer die Extrusionstechnik, Melle (DE)

(72) Inventor: Marius Thiel, Osnabrueck (DE)

(73) Assignee: INOEX GmbH Innovationen und Ausruestungen fuer die Extrusionstechnik, Melle (DE)

( * ) Notice: Subject to any disclaimer, the term of this patent is extended or adjusted under 35 U.S.C. 154(b) by 0 days.

(21) Appl. No.: 16/093,186

(22) PCT Filed: Apr. 6, 2017

(86) PCT No.: PCT/DE2017/100271
§ 371 (c)(1),
(2) Date: Oct. 12, 2018

(87) PCT Pub. No.: WO2017/178009
PCT Pub. Date: Oct. 19, 2017

(65) Prior Publication Data
US 2019/0107485 A1    Apr. 11, 2019

(30) Foreign Application Priority Data
Apr. 14, 2016 (DE) .................. 10 2016 105 599

(51) Int. Cl.
*G01N 21/35* (2014.01)
*G01N 21/3581* (2014.01)
(Continued)

(52) U.S. Cl.
CPC ......... *G01N 21/3581* (2013.01); *G01B 11/06* (2013.01); *G01B 11/24* (2013.01); *G01N 21/8806* (2013.01)

(58) Field of Classification Search
CPC ..... G01N 21/3563; G01N 21/552; G01J 5/10; G01J 5/58
See application file for complete search history.

(56) References Cited

U.S. PATENT DOCUMENTS

2003/0149346 A1*  8/2003  Arnone ............ A61B 5/05
                                                        600/309
2005/0098728 A1*  5/2005  Alfano ............ G01N 21/3581
                                                        250/341.8
(Continued)

FOREIGN PATENT DOCUMENTS

DE      10 2010 010285 A1      9/2011

OTHER PUBLICATIONS

Karpowicz et al., Comparison between pulsed terahertz time-domain imaging and continuous wave terahertz imaging. In: Semiconductor Science and Technology, vol. 20, 2005, pp. S293-S299.
(Continued)

*Primary Examiner* — David P Porta
*Assistant Examiner* — Mamadou Faye
(74) *Attorney, Agent, or Firm* — Collard & Roe, P.C.

(57) ABSTRACT

The invention relates to a terahertz measuring device (1) for measuring a test object (7), comprising:
a THz transmitter and receiver unit (2) for emitting terahertz radiation (3) at a spatial angle of emittance (4) along an optical axis (A), receiving reflected terahertz radiation (8) and generating a signal amplitude (S) as a function of the time or frequency (t, f), and
a controller and evaluator device (12) for receiving and evaluating the signal amplitude (S).
Hereby, the controller and evaluator device (12) determines defects (10, 110) of the test object (7) from the signal amplitude (S). In particular, it is possible to mask a core area (4a) of the emitted terahertz radiation (3).

(Continued)

Figure 3:
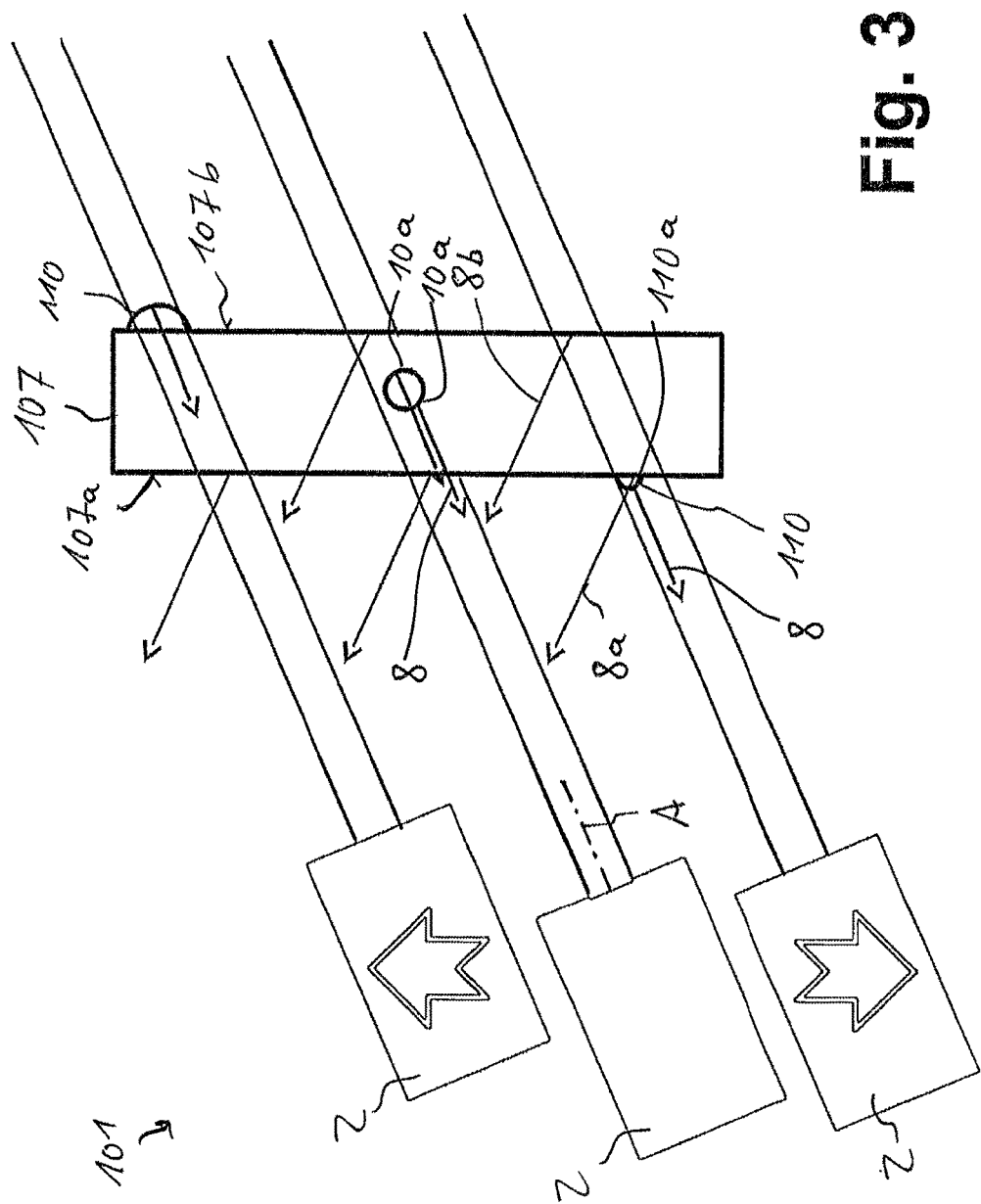

An alternative measuring arrangement can reveal defects also by injecting the THz radiation at a right angle in that additional measuring peaks are detected which cannot be associated with the layer thickness measurement as such.

23 Claims, 8 Drawing Sheets

(51) Int. Cl.
    *G01B 11/24*     (2006.01)
    *G01N 21/88*     (2006.01)
    *G01B 11/06*     (2006.01)

(56) References Cited

U.S. PATENT DOCUMENTS

2013/0048859 A1*   2/2013   Scheller ............. G01N 21/3586
                                                            250/339.08
2015/0211934 A1     7/2015   Van Mechelen et al.
2018/0335465 A1*   11/2018   Xie ....................... G01R 31/11

OTHER PUBLICATIONS

International Search Report of PCT/DE2017/100271, dated Jul. 13, 2017.

* cited by examiner

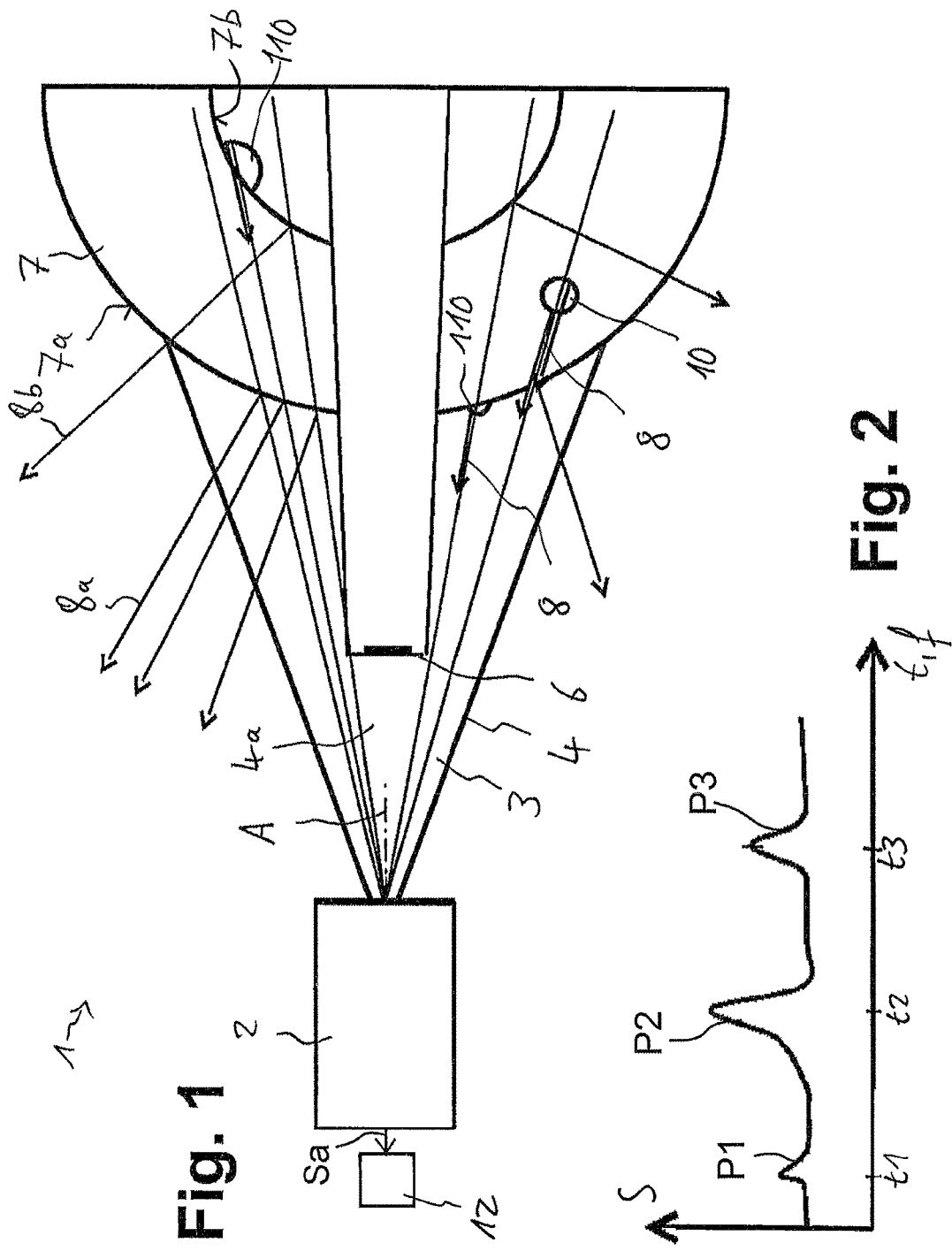

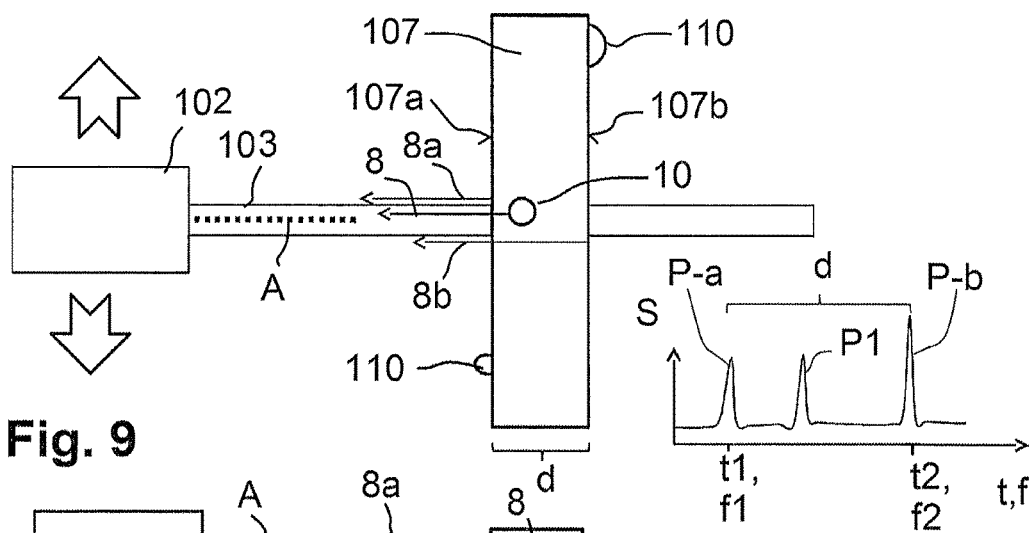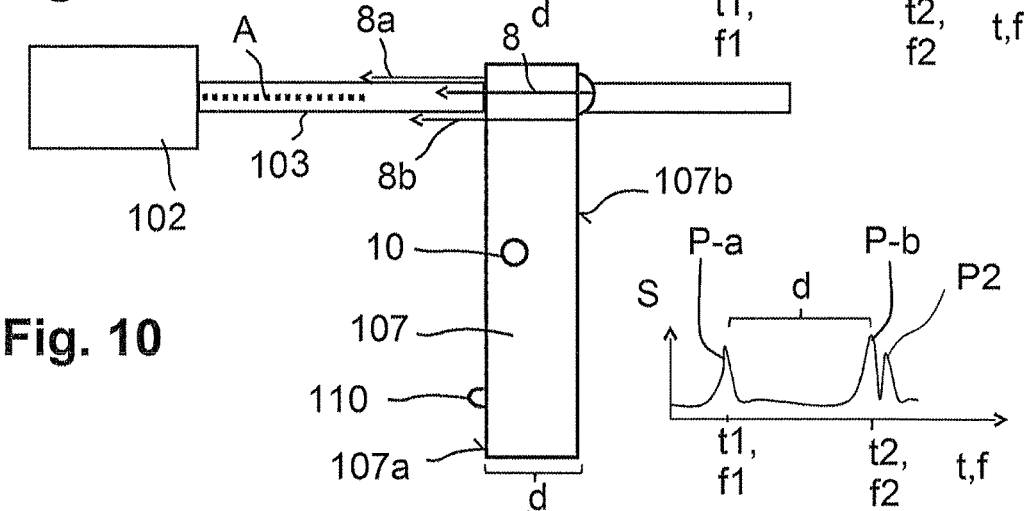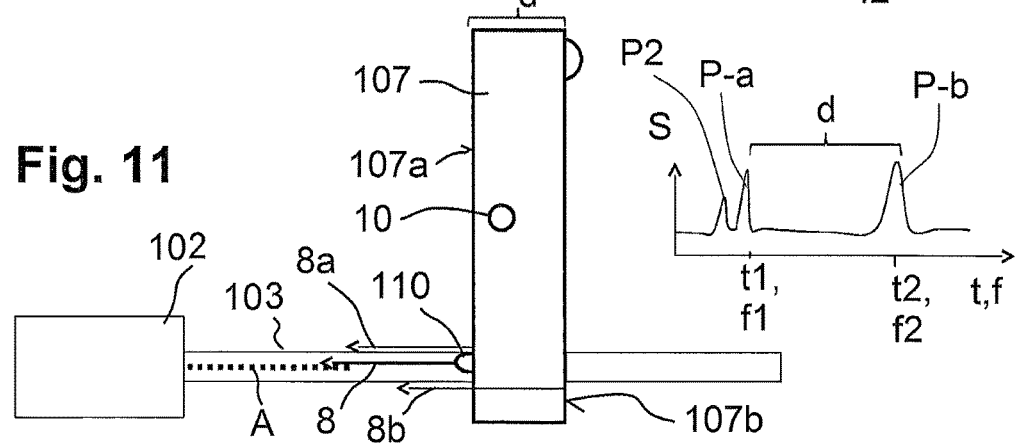

TERAHERTZ MEASURING APPARATUS FOR MEASURING TEST OBJECT AND A TERAHERTZ MEASUREMENT METHOD

CROSS REFERENCE TO RELATED APPLICATIONS

This application is the National Stage of PCT/DE2017/100271 filed on Apr. 6, 2017, which claims priority under 35 U.S.C. § 119 of German Application No. 10 2016 105 599.9 filed on Apr. 14, 2016, the disclosure of which is incorporated by reference. The international application under PCT article 21(2) was not published in English.

The invention relates to a terahertz measuring apparatus for measuring test objects as well as a terahertz measuring method.

Terahertz measuring method allow test objects made of e.g. plastics, paper, earthenware as well as china etc. to be examined without direct contact with the test object. In run-time measurements, terahertz radiation is irradiated onto a test object and the radiation partially reflected each on boundary surfaces between layers having differing refraction indices is measured so that run-time differences of the reflected radiations can be used to determine layer thicknesses.

To that end, generally, a transmitter and receiver unit directs the terahertz radiation in a transmitter emitted cone (spatial angle of emittance) along an optical axis onto the test object whereby the optical axis is arranged perpendicular in relation to the boundary surfaces so that the reflected terahertz radiation is beamed along the optical axis back to the terahertz transmitter and receiver unit.

In order to capture test objects completely, several terahertz transmitter and receiver units may be positioned around the test object or the terahertz transmitter and receiver unit may be moved relative to the test object.

It has become apparent, however, that besides the ordinary measuring peaks of the boundary surfaces, that are used to determine the, there are still disturbances being detected which can compromise the measuring results of the layer thickness measurement.

Furthermore, ultra sound measurements are known, inter alia, for detecting shrink holes or entrapped air in test objects, being used to detect faulty test objects.

The invention is based on the object of creating a terahertz measuring device and a terahertz measuring method for measuring a test object which allow high quality measurements with relatively little expenditure.

This task is solved by a terahertz measuring device according to one aspect of the invention and a terahertz measuring method according to another aspect of the invention. Preferred further developments are described below.

Thus, according to the invention that the terahertz radiation can be used also to selectively detect defects in the test object. To that end, preferably, reflections of the terahertz radiation are detected that are not generated by reflection of the emitted terahertz radiation on the ordinary boundary surfaces layer boundaries respectively.

Hereby, according to the invention, it is recognized that defects, e.g. shrink holes or trapped air or gas respectively in the material of the test object, material accumulations or blisters can lead to local boundary surfaces on the upper and bottom sides of the test object, in particular to curved or closed surfaces each having regions extending perpendicular to the incident terahertz radiation so that they can be detected by measuring the reflected terahertz radiation under varying angles or incidence. Thus, for example, shrink holes generally form spherically closed surfaces such as spheres, ellipsoids of revolution or lenticular areas which can be subject to measurements by reflection, often even both on a front side and a back side of the shrink hole.

To that end, according to one embodiment, are core area of the emitted terahertz radiation around the optical axis is masked by a blind so that terahertz radiation is radiated onto the test object only in a transmitter emitted cone around the blind. Hereby, the terahertz radiation is irradiated onto the boundary surfaces at an angle that is not a right angle so that reflections coming from the test object and directed towards the transmitter and receiver unit may occur only on defects or faults in the test object.

Thus, such a design creates the advantage of a simple to make device with little additional expenditure, e.g. by means of an additional blind making the high measuring peak of the reflection on the boundary surfaces used for layer thickness measurements disappear thereby allowing lower measuring peaks to be detected.

The measuring for defects can also be combined with a measuring layer thicknesses of the test object in that e.g. the blind is adjustable between an active blind position for masking the core are and a passive, retracted position in which the blind is either completely removed from the transmitter emitted cone of the terahertz radiation or e.g. folded into a flat position. Thus, it is possible to detect both layer thicknesses and defects.

According to another embodiment the terahertz radiation is irradiated onto the boundary surfaces at an angle of incidence that is not a right angle so that the main reflections are not reflected back along the optical axis but reflected away from the terahertz transmitter and receiver unit. Thus, in this case, too, detected reflected terahertz radiation can be associated with defects in the test object. Here, too, the expenditure in components is small because merely an adjustment of the optical axis is required.

Hereby, instead of an adjustment of the entire terahertz transmitter and receiver unit, it is possible to adjust a downstream optics, e.g. a pivoting mirror. Thus, the mirror can be adjusted e.g. between a measuring position for measuring a layer thickness and a measuring position for measuring defects so that here, too, a combination of both measurements is possible.

Thus, by excluding or masking the main reflections radiation of the test object by means of a blind or by selecting an angle of incidence of the optical axis that is not a right angle, the received signal amplitude can subsequently be examined selectively for smaller measuring peaks which can, therefore, be clearly associated with defects.

Advantageously, the measuring process is carried out under several angles or positions around the test object so that defects or shrink holes with differing orientations can be detected.

According to a further embodiment always one terahertz transmitter and receiver unit according to the invention can be arranged opposite of a standard terahertz transmitter and receiver unit for measuring the layer thickness of the test object. Hereby, the blind in the optical axis of the terahertz transmitter and receiver unit according to the invention, which masks a core are of the terahertz radiation around the optical axis, can ascertain no direct irradiation happens in the opposite standard terahertz transmitter and receiver unit; thus, the standard terahertz transmitter and receiver unit can examine the layer thickness of the test object by means of a run-time measurement within its core area around the optical axis. Advantageously, the standard terahertz transmitter and receiver unit radiates and detects only in the area masked by the blind so that it does not even detect any scattered radiation of the terahertz transmitter and receiver unit as a signal.

This embodiment may be further provided with a mirror in the core area of the blind, in particular, on the back side of the blind, which mirror hence reflects back the (second) optical axis of the standard terahertz transmitter and receiver unit. Thus, the radiation emitted by the standard terahertz transmitter and receiver unit can first run through the test object entirely and subsequently by reflected totally be the mirror so that this totally reflected terahertz radiation can subsequently be reflected on the boundary surfaces and, following another total reflection on the mirror, is reflected back again to the standard terahertz transmitter and receiver unit. Thus, it is possible to carry out revers scans of the test object in which the boundary surfaces are irradiated from both sides and the measuring peaks around the total reflection peaks around the mirror can be compared to each other in order to be able to measure e.g. finer layer thicknesses or thinner layers respectively.

Thus, synergistic combinations of the blind with mirrors are possible so that the opposite transmitter and receiver units not only do not interfere with each other but the expenditure in components are be utilised twofold.

Furthermore, advantageously, it is possible to precisely determine the position of defects and, thereby, also the size or shape of defects in that terahertz radiation is radiated onto the test object and received by means of several terahertz transmitter and receiver units or, respectively, from different angles and the quantity of position points determined in this way are subtended. Thus, are measurement of the test object around its entire circumference and completely by irradiation from several sides or angles can be combined with the determination of exact positions.

A further embodiment allows a combination of layer thickness measurements with the determination of defects in that the measuring peaks of the defects appear in den signal diagrams in addition to the ordinary measuring peaks of the boundary surfaces. Hereby, the ordinary measuring peaks can be recognized from a comparison with previous and subsequent measurements or from a comparison with the ordinary layer thickness, or the appearance of additional measuring peaks can already lead to an error signal. Thus, this embodiment can be combined, in particular, also with the other embodiments. In such an embodiment, the ordinary measuring peaks in the signal amplitude can be masked by suitable masking regions in order to allow a secure and simple evaluation for defects without physically masking the THz beam in the measuring device.

The measuring device according to the invention can be utilized, in particular, for carrying out the measuring method according to the invention; the measuring method according to the invention can be carried out, in particular, using the measuring device according to the invention.

Thus, according to the invention, it is possible to carry out complete measurements of test objects both for layer thicknesses or, respectively, proper formation and for defects, in particular, including the position and/or size and/or forming, with small expenditure in terms of components.

Figure 4:
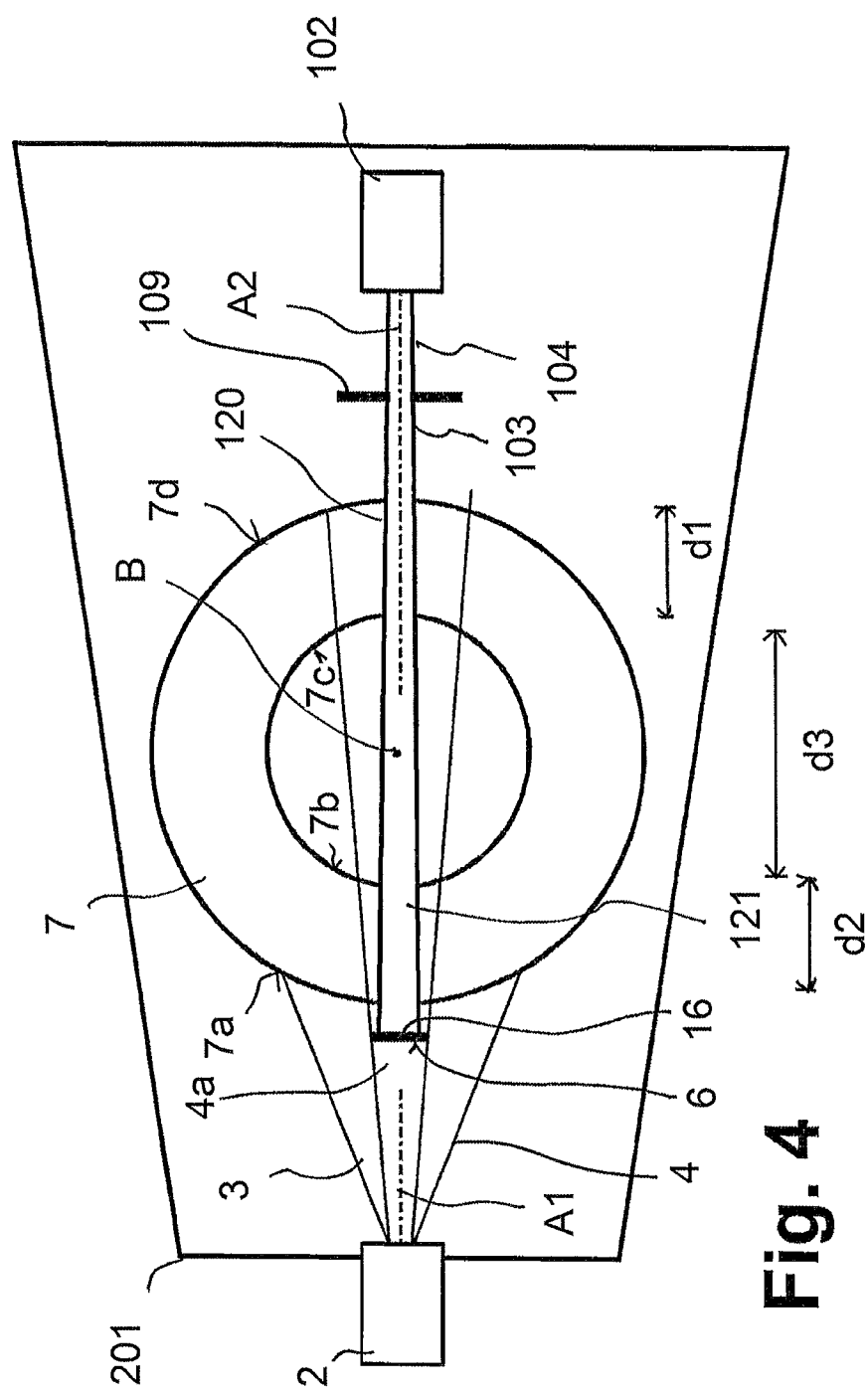
Figure 5:
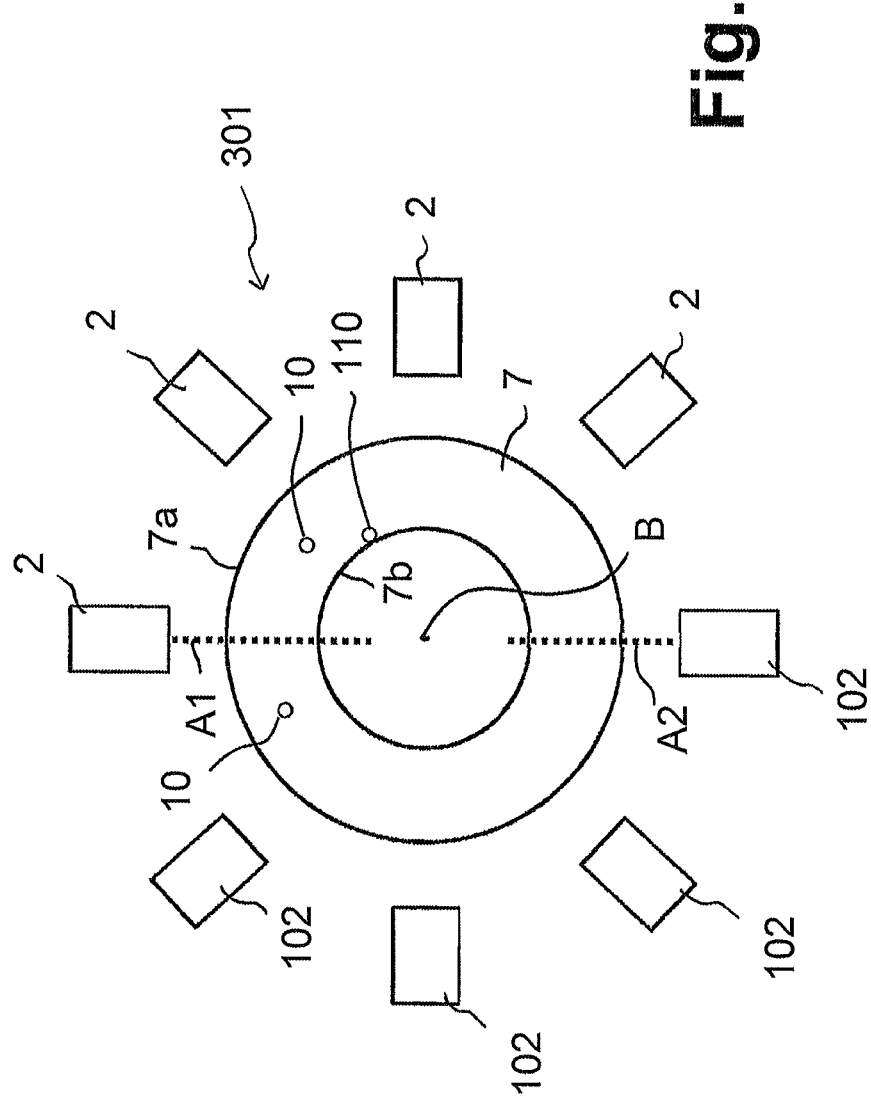
Figure 6:
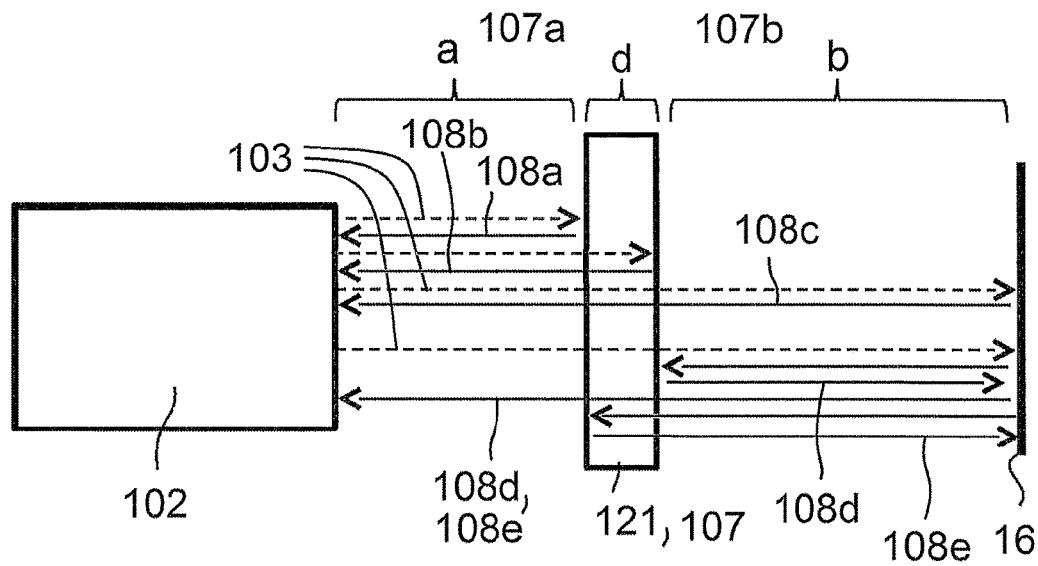
Figure 7:
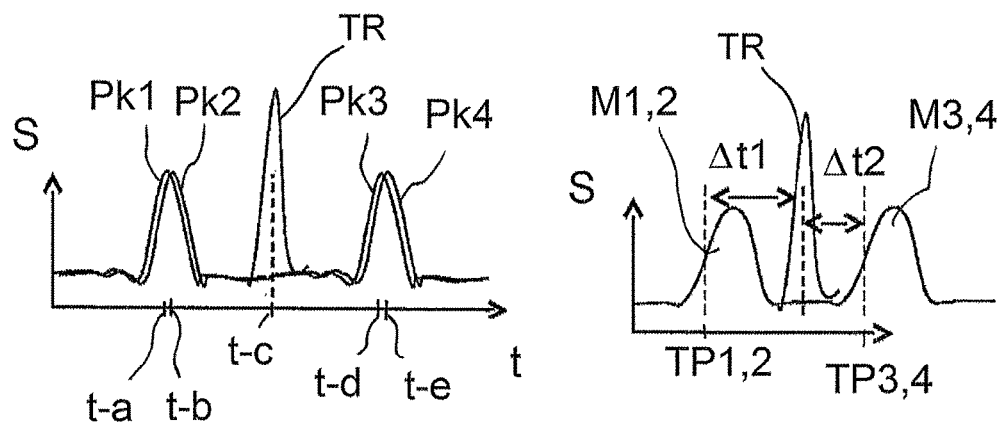
Figure 8:
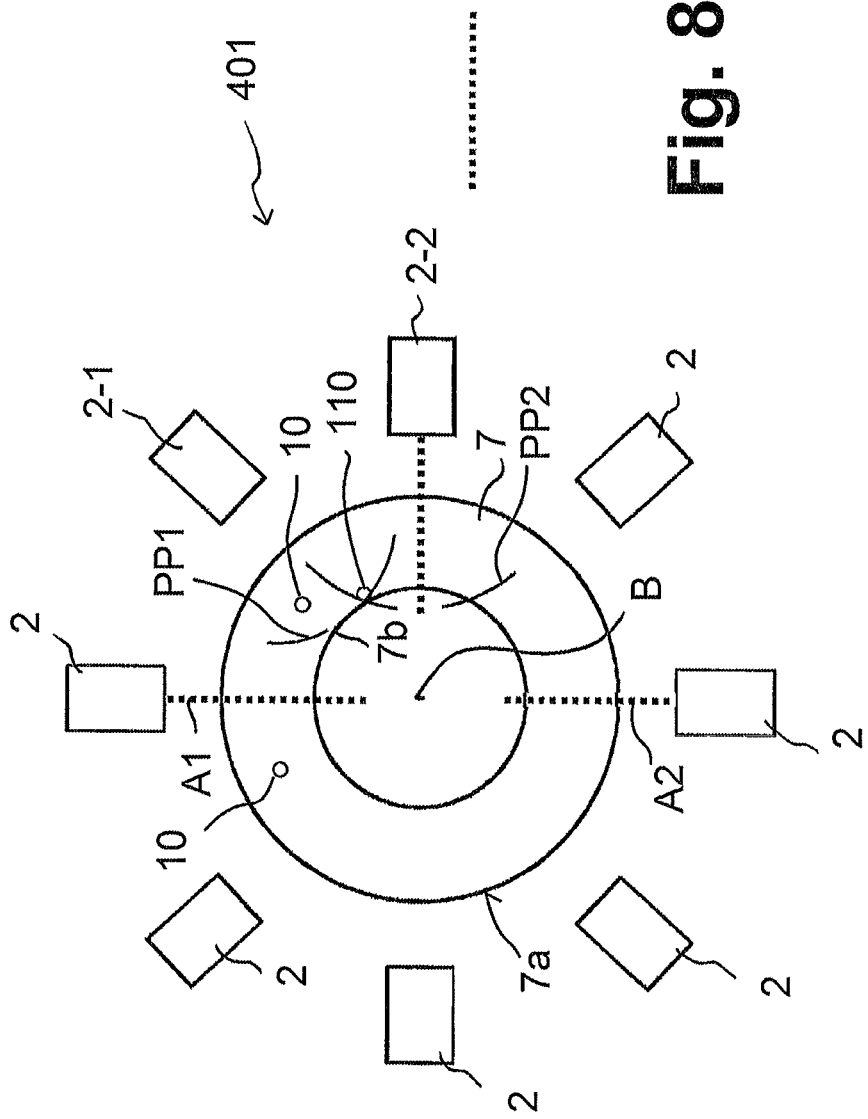
Figure 12:
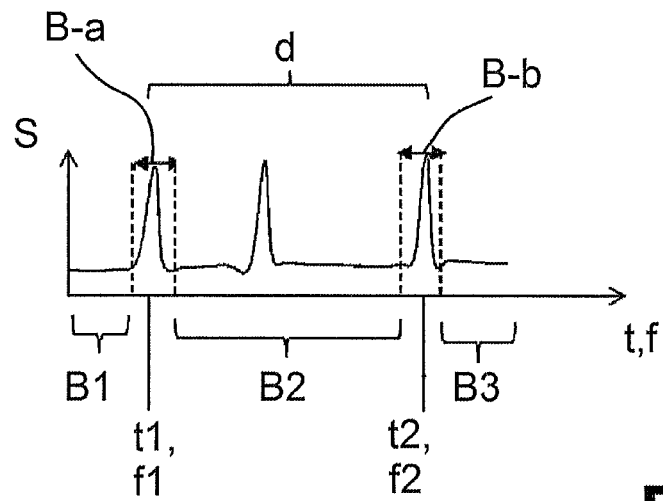
Figure 13:
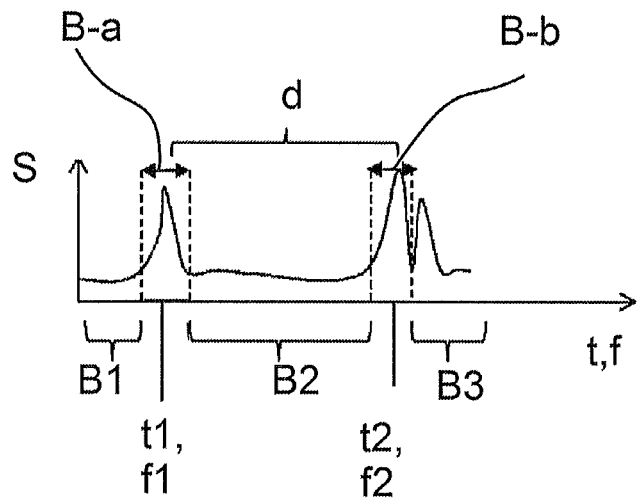
Figure 14:
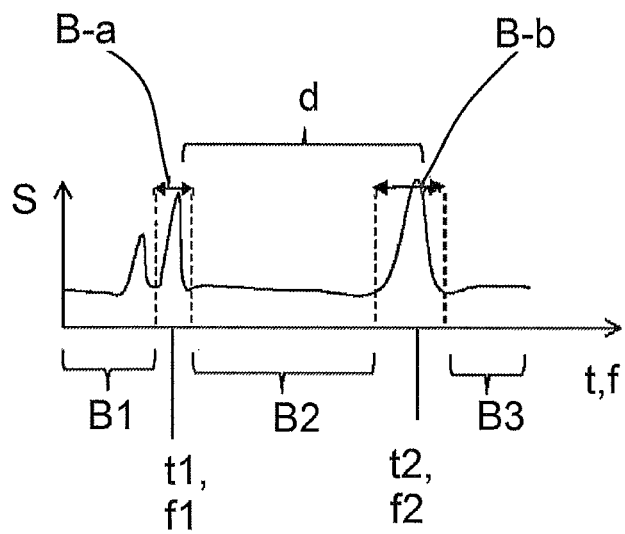

Subsequently, the invention is further illustrated by means of the accompanying drawing in several embodiments. These show in:

FIG. 1 a terahertz measuring device according to an embodiment when measuring a pipe with defects;

FIG. 2 the measuring diagram of the measuring device from FIG. 1;

FIG. 3 a terahertz measuring device according to a further embodiment with angles of incidence that are not right angles, when measuring a flat sample with defects;

FIG. 4 a terahertz measuring device according to a further embodiment with two opposing transmitter and receiver units;

FIG. 5 a further terahertz measuring device according to FIG. 4 with several transmitter and receiver units;

FIG. 6 a representation of the beam paths occurring in the measuring principle of reverse scanning;

FIG. 7 Signal diagrams of the reverse scanning:
a) idealised partial peaks and b) measuring peaks; and FIG. 8 a terahertz measuring device for measuring the entire circumference and determining positions of defects;

FIG. 9 through 11 a terahertz measuring device according to an embodiment for measuring a sample with defects;

FIG. 12 through 14 a technical measurement evaluation of signal amplitudes.

According to FIG. 1, a terahertz measuring device 1 comprises a transmitter and receiver unit 2 for emitting terahertz radiation 3 within an opening cone or spatial angle of emittances 4 along an optical axis A. Hereby, the terahertz measuring device 1 transmits the terahertz radiation 3 preferably within a frequency range of 10 GHz to 10 THz, in particular, from 100 GHz to 3 THz. Hereby, the terahertz transmitter and receiver unit 2 can be designed, in particular fully electronically, i.e. with a transmitter dipole and a receiver dipole; however, optical or electronic-optical transmitter and receiver units 2 are also possible.

In the optical axis A a blind 6 is provided which e.g. absorbs the incident terahertz radiation 3 or—in a manner not shown—reflects the same at an angle other than a right angle or, respectively, not back to the transmitter and receiver unit 2.

The terahertz measuring device 1 made up of the terahertz transmitter and receiver unit 2 and the blind 6 serves for measuring a test object 7, in this case a pipe having a cylindrical—i.e. round in the sectional plane—outer side 7a and a correspondingly concentric inner face 7b. Hereby, test objects 7 made of a material permeable to the terahertz radiation 3 such as plastics, fibre-reinforced plastics (GFK, CFK), ceramics, paper, glass, rubber and also combinations of these materials can be measured whereby the materials each have a refraction index n7 which differs from the refraction index n0 of the environment (air) with n0=1. Plastic materials usually exhibit a refraction index of about n7=1.5. Thus, the incident terahertz radiation 3 essentially passes through the outer side 7a (front side) and the inner face (back side) 7b of the test object 7 with a small fraction of the intensity of e.g. about 4% being reflected on the boundary surface between the media with differing refraction indices so that THz radiation 8 is reflected. Thus, first reflected radiation 8a is reflected on the outer side 7a, second reflected THz radiation 8b on the inner face 7b. Hereby, repeated reflections are ignored because their intensity is very small.

Because the blind 6 shadows a core area 4a of the spatial angle of emittances 4, with such a convexly arched test object 7 or even a planar test object, the first reflected radiation 8a and the second reflected radiation 8b on den ordinary boundary surfaces, i.e. an ordinary cylindrical outer side 7a and ordinary cylindrical inner face 7b is not reflected back to the transmitter and receiver unit 2.

In the test object 7 defects 10, 110 are potentially present on the surfaces 7a, 7b and/or in the material which may be, in particular, shrink holes 10, i.e. trapped air, or blisters 110. Such defects 10 may appear, in particular, in an extrusion process and critically influence the quality of the test object 7. In FIG. 1, by way of example, two protruding blisters 110 formed on the surfaces, i.e. on the front side 7a and on the back side 7b as well as a shrink hole (trapped air, air blister) 10 formed inside the material are shown.

As apparent from FIG. 1, reflections of the incident THz radiation 3 appear on the boundary surfaces 10a, 110a of the defects 10, 110. It is also apparent, in particular, that such blisters 110 or shrink holes 10 are formed curved in a totally or partially closed way so that mostly areas on their boundary surfaces 10a, 110a appear whose normal lies essentially parallel to the incident THz radiation 3 so that a reflection back to the THz transmitter and receiver unit 2 occurs.

FIG. 2 shows a Signal diagram, i.e. the signal amplitude S(t) of the received THz radiation 8 as a function of the time t, or in e.g. a fully electronic system with FM modulation (frequency modulation) as a function of the frequency f or time t. According to FIG. 2, a controller and evaluator unit 12 recognises that the points in time t1, t2, t3, or corresponding frequency values represent invalid measuring peaks P1, P2, P3, i.e. reflections on defects 10, 110 and, therefore, the test object 7 is faulty. Thus, the controller and evaluator unit 12 can put out an error signal.

Also, the distances d10, d110 of the defects 10, 110 can be classified at least approximately by means of a run-time calculation. It is not yet possible to carry out a more accurate localization of a defect 10, 110 by means of the arrangement according to FIG. 1 using one single THz transmitter and receiver device 2. However, a qualitative determination of a fault is possible already. Also, using the run-time, it is possible to calculate the plausibility by determining that the distance lies within the boundaries of the test object 7, i.e. no reflection behind the test object 7.

Moreover, the width of the measuring peaks P1, P2, P3 can also be evaluated in order to gain information, if applicable, for discriminating the defects 10, 110. Thus, a closed shrink hole 10 generates reflections on its front side and back side and, therewith, a broad measuring peak P2, while the blisters 110 generate reflections merely with their thin layer, i.e. front side and back side closely together, so that smaller peak widths are measured, e.g. as half-widths.

FIG. 3 shows an embodiment of a measuring device 101 in which the optical axis A of the transmitter and receiver device 2 is aligned not at a right angle to the boundary surfaces 107a, 107b of a test object 107, in this case e.g. a flat sample 107, e.g. a sheet foil, having a planar parallel front side 107a and back side 107b. To that end, the entire transmitter and receiver device 2, its measuring head or a suitable upstream optics, e.g. a pivoting mirror, can be adjusted. Advantageously, der transmitter emitted cone is relatively small or narrow respectively in order to avoid incidence at a right angle onto the ordinary boundary surfaces 107a, 107b.

The measuring according to FIG. 3 can occur e.g. after production when transporting the test object 107 in the direction of conveyance and at the speed of conveyance v in that the optical axis A is set angular or, respectively not at a right angle, to the direction of conveyance. Thus, no blind is required to avoid a direct reflection peak of the first THz radiation reflected on the front side 107a and the second THz radiation 8b reflected on the back side 107b.

Thus, the transmitter and receiver unit 2 and the test object 107 are adjusted relative to each other in a direction that is not parallel to the optical axis A, in particular, parallel to the surfaces 107a, 107b. Thus, when measuring a test object 107 after production, in particular, the test object 107 can be conveyed in its direction of conveyance v and measured by means of a transmitter and receiver device fixed in position. Thus, in accordance with the three drawn-in positions, an upper blister 110 at an upper position of the transmitter and receiver device relative to the middle position, and a lower blister 110 at the front side 7a at a lower position in the centre. Thus, again, a signal diagram according to FIG. 2 ensues, where the three defects 10, 110 can be detected at different point in time t1, t2 and t3. Hereby, the temporal distance between the spots t1, t2 and t3 depends, in particular, on the conveyance process or, respectively, the adjustment speed of the test object 107 and/or the adjustment speed of the transmitter and receiver device 2.

FIG. 4 shows an embodiment of a measuring-device 201, where a transmitter and receiver device 2 according to FIG. 1, 2 and a standard THz transmitter and receiver device 102 are provided at opposite sides in relation to the test object 7 or a test object position 1007. In particular, its two optical axes A1, A2 may coincide thus forming a common optical axis A which, advantageously, intersects a pipe axis B of the test object 7.

The blind 6 of the THz transmitter and receiver device 2 shown on the left side, from its back side, i.e. the side facing the standard THz transmitter and receiver device 102, a mirror 16, which is positioned perpendicular to the optical axis A and, therefore, mirrors it back.

Thus, here, a terahertz measuring device 201 is created where, in addition to the measuring of defects 10, 110, a direct measuring of the test object 7 in a second transmitter emitted cone 104 around the optical axis A2 is provided in order to determine e.g. layer thicknesses of the test object 7. According to the embodiment shown, the second THz radiation 103 emitted by the standard THz transmitter and receiver device 102 screens a right wall area 120 with the boundary surfaces 7d and 7c, and subsequently, following transmission through the den wall area 120, the left wall area 121 formed by the boundary surfaces 7a and 7b, i.e. the front side 7a and the back side 7b. The radiation 103 emitted by the standard THz transmitter and receiver device 2 is subsequently reflected on the mirror 16 and, as a consequence, again runs through the test object 7 through the boundary surfaces 7a, 7b, 7c and 7d and can, thereafter, be detected by the standard THz transmitter and receiver device 102. Hereby, a blind 109 is provided. Which limits the transmitter emitted cone or, respectively, spatial angle of emittance 104 of the standard THz transmitter and receiver device 2 on the mirror 16.

Since also the first blind 6 of the THz transmitter and receiver device 2 serving for detecting defects—in FIG. 4 shown on the left side—limits the spatial angle of emittance 4 of the THz transmitter and receiver device 2 to the outer region and shades the core area 4a, the two THz transmitter and receiver devices 2, 102 do not interfere with each other's detection. Thus, defects 10, 110 in the test object 7 can be detected by the THz transmitter and receiver unit 2 in the manner described above while, at the same time, direct run-time measurements are carried out on the test object 7 in the same optical axis A (A1=A2) by the standard THz transmitter and receiver device 102, i.e., in particular, wall thicknesses may be measured, in this case according to FIG. 4, a first layer thickness or wall thickness d1 in the right-hand wall area 120, a second wall thickness d2 in the left-hand wall area 121, as well as the interior diameter d3 as air gap between the wall areas.

The second blind 109 also helps to avoid the first THz radiation 3 being scattered on defects 10, 110 of the test object 7 and subsequently being scattered towards the second THz transmitter and receiver device 102 to be detected there, which could lead to flawed measurements.

FIG. 5 shows a measuring device 301, in which several THz transmitter and receiver devices 2, 102 are arranged in the peripheral direction or, respectively, diametrically opposite, in particular, in a plane perpendicular in relation to the pipe axis B of the test object or, respectively, to the direction of conveyance of the test object. According to the measuring device 301 in FIG. 5, THz transmitter and receiver devices 2 according to FIGS. 1, 2 can each be arranged on opposite sides to measure defects 10, 110 and standard THz transmitter and receiver devices 102 to measure the wall thicknesses whereby, in that case, e.g. always one pair of opposite THz transmitter and receiver devices 2, 102 carries out measurements while the other two pairs are switched off in order to avoid interference.

Furthermore, according to FIG. 5, interference of the three pairs of opposite THz transmitter and receiver devices 2, 102 may also be avoided by e.g. pulsed radiation, i.e. pulses offset in time in relation to each other.

Thus, the embodiments of FIGS. 4 and 5 allow simultaneous measuring of both ordinary layer thicknesses d1, d2, d3. Since, according to e.g. FIG. 5, defects 10, 110 can be determined from three different angles of incidence, it is also ensured that each defect 10, 110 has at least one spot or reflective surface respectively that leads to a corresponding received signal at at least one of the three THz transmitter and receiver devices 2.

The special design of the standard THz transmitter and receiver device 102 according to FIGS. 4 and 5 allows, in particular, also layer thicknesses to be measured by a reverse scan, using the following measuring principle:

The special design of the standard THz transmitter and receiver device 102 according to FIGS. 4 and 5 allows, in particular, also layer thicknesses to be measured by a reverse scan, using a measuring principle of FIGS. 6, 7, shown here on the sheet foil 107 and which is correspondingly valid for e.g. the wall areas 120, 121 gilt.

As can be seen from FIG. 6, the THz transmission beam 103, subsequent to the forerun a, falls onto the front side 107*a* of the test object 107, with the front side 107*a* forming a boundary surface from the environment, i.e. the medium air having a refraction index n0=1, to the test object 107 being an optically denser medium, in the case of plastics, for example, n7=1.5. Upon transition or, respectively, upon entry to the front side 107*a* a first reflection beam 108*a* is reflected back to the standard terahertz transmitter and receiver unit 102 which, therefore, travels from the standard terahertz transmitter and receiver unit 102 and after reflection on the front side 107*a* back a total distance of 2·a and is detected, in the idealised signal diagram a) of FIG. 7, at t-a. The share of the radiation reflected in such a border transition is about 4% of the intensity or the signal amplitude so that a large share of the emitted radiation 103 passes into the test object 107 to be subsequently partially reflected in turn on the back side 107*b* of the test object 107 so that at the point in time t-b a second reflection beam 108*b* is detected.

The transmission beam 103 passing through the test object 107 is subsequently totally reflected on the mirror 16 leading, in the signal diagram of FIG. 7*a*), to a very strong total reflection peak TR, shown in schematically reduced size here, at the point in time t-c.

Subsequent to the mirror path b, the re-reflected total reflection beam 108*c* falls onto the back side 107*b* of the test object 107, whereby, with this boundary surface entrance too, a reflection beam 108*b* is generated. Subsequently, the total reflection beam 108*c*, upon passing through the front side 107*a*, generates a further reflection beam 108*e*.

The reflection beams 108*d* and 108*e* reach the mirror 16 where they are being reflected back to pass through the die layer 107 to reach the terahertz transmitter and receiver unit 102 where they are detected at the points in time t-d and t-e.

Hereby, multiple reflections on the boundary surfaces 107*a*, 107*b* are always disregarded because they lead to very small contributions in intensity which are ignored here.

Thus, basically, what follows is the idealised measuring diagram of FIG. 7 *a*) where the two first, directly reflected reflection peaks Pk1 and Pk2 of the emitted transmission radiation 103 occur at the points in time t-a and t-b, subsequently at t-c the more intensive total reflection peak TR and subsequently at the points in time t-d and t-e the reflection peaks Pk3, Pk4 having been reflected twice on the mirror 16 which are generated upon backwards entry into the layer 107 as well as exist from the layer 107. The run-time difference between t-a and t-b as well as between t-d and t-e represents the layer thickness d which can be calculated under consideration of the speed of light c and the refraction index n7.

Owing to the smaller layer thickness d and the lower accuracy to be attained, which depends e.g. on the bandwidth and measuring accuracy, the superimposed (merging) reflection peaks Pk1 and Pk2 at the points in time t-a and t-b as well as the reflection peaks Pk3 and Pk4 at the points in time t-d and t-e are too wide and, therefore, cannot be separated; what can be measured is merely, according to FIG. 7 *b*), a first measuring peak M1,2 of the front side radiation incidence occurring prior to the total reflection peak TR and a second measuring peak M3,4 of the back side radiation incidence occurring after the total reflection peak TR. The total reflection peak Tr itself can be with high precision due to its high intensity so that even its middle point in time t-c can be determined precisely.

The measuring peaks M1,2 and M3,4 exhibit different temporal distances Δt1, Δt2 to the total reflection peak Tr, in particular, when comparing each of their leading edges or each of their tailing edges to the temporal mean value t–c of the total reflection peaks Tr, whereby Δt1>Δt2. Thus, information on the layer thickness d, in particular, including the layer thickness d itself, can be derived from the difference Δt1−Δt2; considering the refraction index n7 in the layer 107 and the speed of light in a vacuum vc the following is true:

$$d=(\Delta t1-\Delta t2)*½*vc/n6$$

Thus, according to the invention, a complete and highly precise examination both for defects 10, 110 and the layer thicknesses d, d1, d2, d3 is rendered possible.

Furthermore, in all embodiments it is possible to determine the position, size and/or shape of the defects 10, 110 by arranging several THz transmitter and receiver units 2 around the test object 7, 107, as shown with the THz measuring device 401 according to FIG. 8; this determination is, in particular, also possible in the embodiment of FIG. 5.

According to FIG. 8, each THz transmitter and receiver unit 2 determines one quantity of position points in relation to an impurity 10 or 110. This is shown in FIG. 8, by way of example, for a first THz transmitter and receiver unit 2-1, which in this case determines the first quantity of position points PP1, encompassing points having approximately equal run-times. Ideally, these lie on a spherical shell around the first THz transmitter and receiver unit 2-1 whereby the differing run-times in the sample 7 and in the air may generally lead to a somewhat different distribution of shaping of the quantity of position points PP1. Since a core area around the optical axis remains exempted the quantity of position points PP1 thus forms e.g. a ring area. Accordingly, the second THz transmitter and receiver unit 2-2 determines a second quantity of position points PP2 etc., whereupon the quantity of position points PP1, PP2, PP3 can subsequently be intersected making the localization of the position more precise. Thus, it is possible to also determine the size and/or shaping of the impurities 10 or 110. The central determination can happen in the controller device of one of the THz transmitter and receiver units 2.

According to the embodiment of FIGS. 9 through 11, the measuring of defects 10, 110 happens together with the layer thickness measurement. To that end the THz transmitter and receiver unit 102 emits terahertz radiation 103 along the optical axis A at a right angle onto the boundary surfaces, e.g. a front side 107a and a back side 107b, of a sample, in this case e.g. a sample 107. Thus, a first terahertz radiation 8a, which is detected by the THz transmitter and receiver unit 102 at the point in time t1 as the anterior measuring peak P-a of the signal amplitude S(t), is reflected on the front side 107a, and on der back side 107b a second terahertz radiation 8b is reflected, which is detected by the THz transmitter and receiver unit 102 at the point in time t2 as the posterior measuring peak P-b of the signal amplitude S(t). Thus, it is possible to carry out a run-time measurement for determining the layer thickness d of the flat sample 107 from the measured values t2-t1 and knowledge of the refraction index n107 of the material of the flat sample 107.

The sample 107 is measured by relative adjustment of the THz transmitter and receiver unit 102 in relation to the sample 107, as indicated in FIG. 1 by the arrows, resulting in the measuring situations of the FIGS. 9, 10, 11. Thus, continuously or repeatedly respectively layer thicknesses measurements are taken by emitting terahertz radiation 103 and measuring the run-times t1 and t2.

Defects 10, 110 lead to defect measuring peaks P1, P2 in the signal diagrams of the FIGS. 9, 10 and 11. Recognition of the defects-measuring peaks P1, P2 and discrimination from the anterior and posterior measuring peaks P-a and P-b happens preferable by means of comparing sequential measurements because, in addition to the measuring peaks P-a and P-b, one or more further measuring peaks P1, P2 appear, or an error signal is created already upon recognition of more than two measuring peaks.

Measuring and determining defects according to FIGS. 9 through 11 may be couples with the further embodiment; thus, in the embodiment of FIG. 1, 2, it is possible to e.g. alternatingly open and close a blind 6. Also, the blind may e.g. rotate, in particular, about a blind axis so that is being opened and closed alternatingly during a continuous rotation movement.

The FIGS. 12, 13, 14 show advantageous technical measurement evaluations of the signal amplitudes S of the FIGS. 9, 10, 11, whereby a technical measurement masking or, respectively "electronic masking" is carried out: masking regions B-a, B-b, i.e. frequency regions or runt-time regions in which no evaluation for defects is carried out, are defined always in der signal amplitude S around the ordinary anterior and posterior measuring peaks P-a and P-b, i.e. around their time value t1, t2 or frequency value f1, f2. Thus, only the evaluation regions B1, B2, B3 outside the masking regions B-a, B-b, in which measuring peaks P1, P2, P3 of the defects are determined, remain in the signal amplitude S.

Thus, in particular, combinations of the different embodiments allow a precise measurement whereby the position can be determined precisely by means of measuring from different angles.

The invention claimed is:

1. A terahertz measuring device for measuring a test object, said terahertz measuring device comprising:
   a THz transmitter and receiver unit for emitting terahertz radiation at a spatial angle of emittance along an optical axis, receiving reflected terahertz radiation and generating a signal amplitude as a function of the time or frequency;
   a controller and evaluator device for receiving and evaluating said signal amplitude; and
   a blind positioned or capable of being positioned in the optical axis for masking a core area of the spatial angle of emittances around the optical axis;
   wherein the controller and evaluator device determines defects of the test object from said signal amplitude.

2. The terahertz measuring device according to claim 1, wherein said THz transmitter and receiver unit is configured or adapted to receive reflected terahertz radiation which has not been reflected at a right angle on ordinary boundary surfaces of the test object.

3. The terahertz measuring device according to claim 1, wherein the blind can be adjusted between an active position for shielding the core area and a passive position for passing the core are.

4. The terahertz measuring device according to claim 1, wherein the controller and evaluator device assesses measuring peaks in the received, reflected terahertz radiation as reflections on defects of the test object and puts out an error signal in the event that a sufficiently high measuring peak is detected.

5. The terahertz measuring device according to claim 1, wherein a standard terahertz transmitter and receiver unit is provided for emitting terahertz radiation within a second core area around its second optical axis and for determining a layer thickness of the test object by means of a run-time measurement with determination of reflections on ordinary boundary surfaces as measuring peaks of a received signal amplitude whereby a defect is detected as at least one additional measuring peak.

6. The terahertz measuring device according to claim 1, wherein the THz transmitter and receiver unit comprises terahertz radiation within a frequency range of 10 GHz to 10 THz, in particular 100 GHz to 3 THz, in particular fully electronically with a transmitter dipole and a receiver dipole.

7. A terahertz measuring method for measuring a test object, including at least the following steps:
   emitting terahertz radiation onto a test object;
   receiving reflected terahertz radiation and generating a signal amplitude as a function of the time or the frequency; and
   evaluating the signal amplitude whereby reflection peaks in the signal amplitude are assessed as reflections on defects of the test object and, depending on the evaluation, a signal, e.g. an error signal and/or position signal, is put out;
   wherein, in a received signal amplitude, masking regions, e.g. frequency ranges or run-time ranges, of measuring peaks of reflections on ordinary boundary surfaces are defined, and these masking regions are masked or rejected for the determination of the reflection peaks of the reflections on the defects of the test object so that the reflection peaks are determined outside the masking regions.

8. The terahertz measuring method according to claim 7, wherein terahertz radiation is radiated onto the test object and detected under differing angles.

9. The terahertz measuring method according to claim 7, wherein, for determining a layer thickness of the test object by means of a run-time measurement, terahertz radiation is irradiated onto ordinary boundary surfaces of the test object at a right angle, with detection of the measuring peaks of the boundary surfaces, and a defect is detected as at least one additional measuring peak.

10. The terahertz measuring method according to claim 7, wherein terahertz radiation is emitted and detected within a frequency range of 10 GHz to 10 THz, in particular from 100 GHz to 3 THz, in particular fully electronically.

11. The terahertz measuring method according to claim 7, wherein test objects made of one or more of the following materials are measured:
plastics, fibre-reinforced plastics, earthenware such as e.g. ceramics, paper, glass, rubber.

12. The terahertz measuring method according to claim 11, wherein it is being carried out directly after or during the making of the test object, e.g. after an extrusion.

13. A terahertz measuring device for measuring a test object, said terahertz measuring device comprising:
a THz transmitter and receiver unit for emitting terahertz radiation at a spatial angle of emittance along an optical axis, receiving reflected terahertz radiation and generating a signal amplitude as a function of the time or frequency; and
a controller and evaluator device for receiving and evaluating said signal amplitude;
wherein the controller and evaluator device determines defects of the test object from said signal amplitude;
wherein the controller and evaluator device assesses measuring peaks in the received, reflected terahertz radiation as reflections on defects of the test object and puts out an error signal in the event that a sufficiently high measuring peak is detected; and
wherein the controller and evaluator device defines masking regions of measuring peaks of reflections on ordinary boundary surfaces inside a received signal amplitude, and masks the masking regions or rejects the use of the masking regions for determining the measuring peaks of the reflections on the defects of the test object.

14. A terahertz measuring device for measuring a test object, said terahertz measuring device comprising:
a THz transmitter and receiver unit for emitting terahertz radiation at a spatial angle of emittance along an optical axis, receiving reflected terahertz radiation and generating a signal amplitude as a function of the time or frequency; and
a controller and evaluator device for receiving and evaluating said signal amplitude;
wherein the controller and evaluator device determines defects of the test object from said signal amplitude
wherein a standard terahertz transmitter and receiver unit is provided for emitting terahertz radiation within a second core area around its second optical axis and for determining a layer thickness of the test object by means of a run-time measurement with determination of reflections on ordinary boundary surfaces as measuring peaks of a received signal amplitude whereby a defect is detected as at least one additional measuring peak, and
wherein a Terahertz transmitter and receiver unit and a Standard terahertz transmitter and receiver unit arranged opposite the test object or a test object position are provided, and the second core area lies in the first core area of the terahertz transmitter and receiver unit shaded by a blind of the terahertz transmitter and receiver unit.

15. The terahertz measuring device according to claim 14, wherein the first optical axis of the terahertz transmitter and receiver unit and the second optical axis of the standard terahertz transmitter and receiver unit coincide in total or substantially.

16. The terahertz measuring device according to claim 14, wherein in the core shadow of the blind, e.g. on the backside of the blind, a mirror is provided in the second optical axis of the standard terahertz transmitter and receiver unit whereby the standard terahertz transmitter and receiver unit detects terahertz radiation
terahertz radiation reflected directly at a boundary surface, and
terahertz radiation reflected after total reflection on the mirror, followed reflection on a boundary surface and again total reflection on the mirror.

17. The terahertz measuring device according to claim 14, wherein several, e.g. three, pairs of terahertz transmitter and receiver units and standard terahertz transmitter and receiver units are arranged in the peripheral direction distributed around the test object or a test object position.

18. A terahertz measuring device for measuring a test object, said terahertz measuring device comprising:
a THz transmitter and receiver unit for emitting terahertz radiation at a spatial angle of emittance along an optical axis, receiving reflected terahertz radiation and generating a signal amplitude as a function of the time or frequency; and
a controller and evaluator device for receiving and evaluating said signal amplitude;
wherein the controller and evaluator device determines defects of the test object from said signal amplitude,
wherein several terahertz transmitter and receiver units are arranged distributed around the test object or a test object position and each determine a quantity of position points of one or more defects, and
a central controller and evaluator device is provided, which determines a position and/or size and/or shape of the individual defects from said one or more quantity of position points.

19. A terahertz measuring method for measuring a test object, including at least the following steps:
emitting terahertz radiation onto a test object;
receiving reflected terahertz radiation and generating a signal amplitude as a function of the time or the frequency; and
evaluating the signal amplitude whereby reflection peaks in the signal amplitude are assessed as reflections on defects of the test object and, depending on the evaluation, a signal, e.g. an error signal and/or position signal, is put out;
wherein the terahertz radiation is put out at a spatial angle of emittance along an optical axis and the terahertz radiation is masked in a core area around the optical axis by means of a blind.

20. The terahertz measuring method according to claim 19, wherein for measuring the defects of the test object the blind is adjusted to the active position for shielding the core area and, for carrying out a standard measurement of layer thicknesses of the test object, into a passive position for passing the core area.

21. The terahertz measuring method according to claim 19, wherein the test object is examined for defects from a first side while masking the first core area and, from the opposite second side, layer thicknesses of the test object are measured in a second core area which lies inside the first core area, in particular, using a mirror reflection on a mirror behind the test object for a reverse scan.

22. A terahertz measuring method for measuring a test object, including at least the following steps:

emitting terahertz radiation onto a test object;

receiving reflected terahertz radiation and generating a signal amplitude as a function of the time or the frequency; and evaluating the signal amplitude whereby reflection peaks in the signal amplitude are assessed as reflections on defects of the test object and, depending on the evaluation, a signal, e.g. an error signal and/or position signal, is put out;

wherein the boundary surfaces of the test object are irradiated with the terahertz radiation under an angle of incidence that is not a right angle and main reflections beams reflected on the boundary surfaces of the test object are not reflected to the terahertz transmitter and receiver unit and detected there.

23. A terahertz measuring method for measuring a test object, including at least the following steps:

emitting terahertz radiation onto a test object;

receiving reflected terahertz radiation and generating a signal amplitude as a function of the time or the frequency; and evaluating the signal amplitude whereby reflection peaks in the signal amplitude are assessed as reflections on defects of the test object and, depending on the evaluation, a signal, e.g. an error signal and/or position signal, is put out;

wherein terahertz radiation is emitted and received by several terahertz transmitter and receiver units arranged around the test object whereby each of the terahertz transmitter and receiver units determines a quantity of position points of one or more defects, and a position and/or size and/or shape of the individual defects is determined from said one or more quantity of position points.

* * * * *